US00PP27675P3

(12) United States Plant Patent
Geerlings

(10) Patent No.: US PP27,675 P3
(45) Date of Patent: Feb. 14, 2017

(54) ***PHLOX* PLANT NAMED 'CLEOPATRA'**

(50) Latin Name: *Phlox paniculata*
Varietal Denomination: Cleopatra

(71) Applicant: Peter Geerlings, Hillegom (NL)

(72) Inventor: Peter Geerlings, Hillegom (NL)

(73) Assignee: Compass Plants B.V., Hillegom (NL)

( * ) Notice: Subject to any disclaimer, the term of this patent is extended or adjusted under 35 U.S.C. 154(b) by 93 days.

(21) Appl. No.: 14/545,485

(22) Filed: May 12, 2015

(65) Prior Publication Data

US 2016/0338245 P1 Nov. 17, 2016

(51) Int. Cl.
*A01H 5/02* (2006.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Phlox* plant named 'Cleopatra', characterized by its tall upright plant habit; dark-green colored leaves; freely flowering habit; long flowering period; red purple-colored semi-double flowers; and good cut flower and garden performance.

1 Drawing Sheet

Botanical designation: *Phlox paniculata.*
Cultivar denomination: 'CLEOPATRA'.

BACKGROUND OF THE INVENTION

The present invention relates to a new and distinct cultivar of *Phlox* plant, botanically known as *Phlox paniculata* and hereinafter referred to by the cultivar name 'Cleopatra'.

The new *Phlox* plant originated from a cross-pollination of two unnamed proprietary selections of *Phlox paniculata*, not patented, in 2010. The new *Phlox* was discovered and selected by the Inventor as a single flowering plant from within the progeny of the stated cross-pollination grown in a controlled greenhouse environment in Hillegom, The Netherlands in July, 2012.

Asexual reproduction of the new *Phlox* plant by vegetative cuttings in a controlled greenhouse environment in Hillegom, The Netherlands since February, 2013, has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Cleopatra'. These characteristics in combination distinguish 'Cleopatra' as a new and distinct *Phlox* plant:

1. Tall upright plant habit.
2. Dark-green colored leaves.
3. Freely flowering habit.
4. Long flowering period.
5. Red purple-colored semi-double flowers.
6. Good cut flower and garden performance.

Plants of the new *Phlox* and the parent selections differ primarily in flower form as plants of the parent selections have single-type flowers.

Plants of the new *Phlox* can also be compared to plants of *Phlox paniculata* 'Windsor', not patented. In side-by-side comparisons conducted in Hillegom, The Netherlands, plants of the new *Phlox* and 'Windsor' differed primarily in flower color and form as plants of 'Windsor' had apricot orange-colored single-type flowers. In addition, plants of the new *Phlox* were slightly taller than plants of 'Windsor'.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph is a side perspective view of a typical flowering plant of 'Cleopatra' grown in a container.

DETAILED BOTANICAL DESCRIPTION

The aforementioned photograph and following observations, measurements and values describe plants grown during the summer in an outdoor nursery in Hillegom, The Netherlands and under commercial practices typical of commercial *Phlox* production. During the production of the plants, day temperatures ranged from 16° C. to 32° C. and night temperatures ranged from 6° C. to 18° C. Plants were six months old when the photograph and description were taken. In the following description, color references are made to The Royal Horticultural Society Colour Chart, 2007 Edition, except where general terms of ordinary dictionary significance are used.

Botanical classification: *Phlox paniculata 'Cleopatra'*.

Parentage:

*Female, or seed, parent.*—Unnamed proprietary selection of *Phlox paniculata*, not patented.

*Male, or pollen, parent.*—Unnamed proprietary selection of *Phlox paniculata*, not patented.

Propagation:

*Type.*—By vegetative cuttings.

*Time to initiate roots, summer.*—About three weeks at temperatures about 20° C.

*Root description.*—Fine, fibrous; white in color.

Plant description:

*Plant and growth habit.*—Upright plant habit; narrow inverted triangle; moderately vigorous to vigorous growth habit; basally branching habit.

*Plant height.*—About 55.9 cm.

*Plant width (spread).*—About 21.8 cm.

*Lateral branches.*—Length: About 33.1 cm. Diameter: About 6 mm. Internode length: About 2.5 cm. Strength: Strong. Aspect: Mostly erect. Texture: Smooth, glabrous. Color: Close to 145A.

Leaf description:

*Arrangement.*—Opposite, simple.

*Length.*—About 9.4 cm.

*Width.*—About 2.8 cm.

*Shape.*—Elliptic; moderately concave to convex.

*Apex.*—Long apiculate.

*Base.*—Cuneate to truncate.

*Margin.*—Entire, very slightly revolute.

*Texture, upper and lower surfaces.*—Smooth, glabrous; slightly rugose.

*Luster, upper surface.*—Slightly glossy.

*Luster, lower surface.*—Matte.

*Venation pattern.*—Pinnate.

*Color.*—Developing leaves, upper surface: Slightly darker than between 141A and 143A. Developing leaves, lower surface: Close to 143A. Fully expanded leaves, upper surface: Close to between 137A and N137B; venation, close to 144A. Fully expanded leaves, lower surface: Close to 146B; venation, close to 144C.

*Petioles.*—Length: About 3 mm. Diameter: About 2 mm by 3 mm. Texture, upper and lower surfaces: Smooth, glabrous. Color, upper and lower surfaces: Close to 144C.

Flower description:

*Flower type and flowering habit.*—Semi-double salver-form flowers arranged in compound terminal panicles; flowers face upright and outward; panicles roughly conical in shape; freely flowering habit with about 240 flowers developing per inflorescence.

*Fragrance.*—Moderately fragrant; sweet and pleasant.

*Natural flowering season.*—Long flowering period; plants flower continuously from July through September in The Netherlands.

*Postproduction longevity.*—Flowers last about ten days on the plant; flowers not persistent.

*Flower buds.*—Height: About 2.1 cm. Diameter: About 4 mm. Shape: Narrowly oblanceolate. Color: Sepals, close to N186C; petals, close to 71B.

*Inflorescence height.*—About 23.8 cm.

*Inflorescence diameter.*—About 21.8 cm.

*Flower diameter.*—About 3.5 cm.

*Flower depth.*—About 2.7 cm.

*Petals.*—Quantity per flower: Typically five in a single whorl; lower half of petals fused and forming a narrow tube; each outer petal with two smaller "wing-like" petals. Length, outer petals: About 3.4 cm. Lobe width, outer petals: About 1.1 cm. Length, smaller petals: About 1 cm. Lobe width, smaller petals: About 2 mm. Shape, outer petals: Spatulate. Shape, smaller petals: Lanceolate. Apex, outer and smaller petals: Rounded. Margin, outer and smaller petals: Entire. Texture, outer and smaller petals, upper and lower surfaces: Smooth, glabrous; velvety.

*Color, outer and smaller petals.*—Developing petals, upper surface: Close to 52A to 52B; center, close to 61B; throat, close to 60C. Developing petals, lower surface: Close to 52B and N57B to N57C; tube, close to 60C. Fully developed petals, upper surface: Close to 52A; center, close to 61B; throat, close to 60C; color becoming closer to 58C. Fully developed petals, lower surface: Close to 52C and N57C; tube, close to 60C.

*Sepals.*—Quantity per flower: Typically five in a single whorl, lower half fused and forming a campanulate calyx. Length: About 1 cm. Width: About 1.5 mm. Shape: Lanceolate. Apex: Narrowly apiculate. Margin: Entire. Texture, upper and lower surfaces: Smooth, glabrous. Color, developing and fully expanded sepals, upper surface: Close to 147B; margins, close to N77B. Color, developing and fully expanded sepals, lower surface: Close to N186C; margins, close to N77B.

*Peduncles.*—Length, primary peduncles: About 19.9 cm. Diameter, primary peduncles: About 4 mm. Length, secondary peduncles: About 7.4 cm. Diameter, secondary peduncles: About 2 mm. Aspect, primary peduncles: Erect. Aspect, secondary peduncles: About 45° from vertical. Strength, primary and secondary peduncles: Strong. Texture, primary and secondary peduncles: Smooth, glabrous. Color, primary and secondary peduncls: Close to 145B.

*Pedicels.*—Length: About 6 mm. Diameter: About 1 mm. Aspect: About 40° from peduncle axis. Strength: Strong. Texture: Smooth, glabrous. Color: Close to 146B tinged with close to N186B.

*Reproductive organs.*—Stamens: Quantity per flower: Typically five; filaments fused with petals in throat. Filament length: About 0.5 mm. Filament color: Close to 60D. Anther shape: Oblong. Anther length: About 2 mm. Anther color: Close to 8D. Pollen amount: Scarce. Pollen color: Close to 11D. Pistils: Quantity per flower: One. Pistil length: About 1.6 cm. Stigma shape: Cleft, three-parted. Stigma color: Close to 150D. Style length: About 1.5 cm. Style color: Close to 183D. Ovary color: Close to 144A.

*Seeds and fruits.*—Seed and fruit development have not been observed on plants of the new *Phlox*.

Pathogen & pest resistance: Plants of the *Phlox* have not been observed to be resistant to pathogens and pests common to *Phlox* plants.

Garden performance: Plants of the new *Phlox* have been observed to have good garden performance and tolerate rain, wind, high temperatures about 35° C. and to be hardy to USDA Hardiness Zone 6.

It is claimed:

1. A new and distinct *Phlox* plant named 'Cleopatra' as illustrated and described.

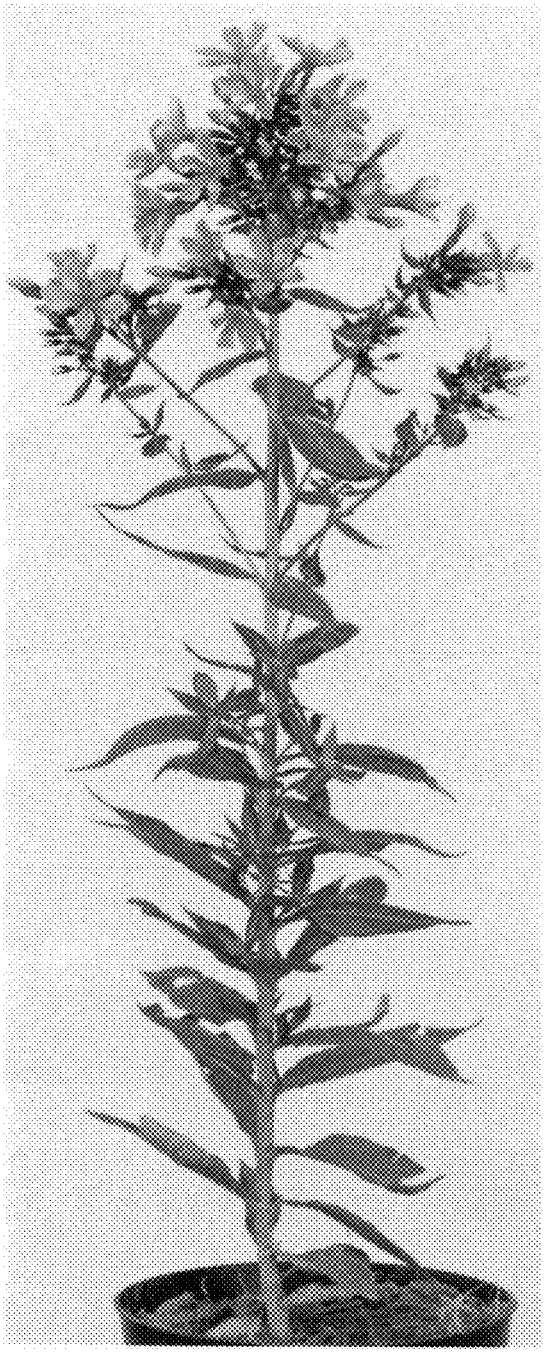

* * * * *